(12) United States Patent
Seguy

(10) Patent No.: US 9,693,759 B2
(45) Date of Patent: Jul. 4, 2017

(54) OPERATING DEVICE WITH A CONTROL HANDLE AND A FLEXIBLE ELEMENT CONNECTED TO THE CONTROL HANDLE

(71) Applicant: COLOPLAST A/S, Humlebaek (DK)

(72) Inventor: Sebastien Seguy, Gourdon (FR)

(73) Assignee: Coloplast A/S, Humlebaek (DK)

( * ) Notice: Subject to any disclaimer, the term of this patent is extended or adjusted under 35 U.S.C. 154(b) by 271 days.

(21) Appl. No.: 14/358,042

(22) PCT Filed: Nov. 16, 2012

(86) PCT No.: PCT/DK2012/050421
§ 371 (c)(1),
(2) Date: May 14, 2014

(87) PCT Pub. No.: WO2013/071938
PCT Pub. Date: May 23, 2013

(65) Prior Publication Data
US 2014/0336532 A1 Nov. 13, 2014

(30) Foreign Application Priority Data
Nov. 16, 2011 (EP) .................................... 11290525

(51) Int. Cl.
*A61B 10/04* (2006.01)
*A61B 17/00* (2006.01)
(Continued)

(52) U.S. Cl.
CPC ........ *A61B 17/00234* (2013.01); *A61B 1/008* (2013.01); *A61B 1/00066* (2013.01);
(Continued)

(58) Field of Classification Search
CPC . A61B 10/06; A61B 10/0266; A61B 10/0275; A61B 10/02; A61B 10/0096
(Continued)

(56) References Cited

U.S. PATENT DOCUMENTS 5,685,823 A 11/1997 Matsuno
5,779,686 A 7/1998 Yanuma
(Continued)

FOREIGN PATENT DOCUMENTS

CN 201079479 Y 7/2008
CN 201879872 U 6/2011
(Continued)

OTHER PUBLICATIONS

Office Action mailed on Mar. 10, 2017 in U.S. Appl. No. 29/563,163.

*Primary Examiner* — Daniel Cerioni
(74) *Attorney, Agent, or Firm* — Coloplast Corp., Coloplast A/S; Nick Baumann

(57) ABSTRACT

This invention relates to an operation device especially intended to proceed with an operation inside the body of a living being. This device (10) comprises a control handle and a flexible element (12) provided with a proximal end connected to this control handle. The flexible element (12) comprises at a distal end (14), a steerable area comprising a rigid head. The control handle comprises a control lever arranged for controlling said steerable area (17) of this flexible element. The device of the invention is characterized in that the flexible element (12) comprises at its distal end (14), a retractable tool (21), and this retractable tool being arranged to be operated by said control handle.

14 Claims, 3 Drawing Sheets

(51) Int. Cl.
*A61B 1/008* (2006.01)
*A61B 1/018* (2006.01)
*A61B 1/00* (2006.01)
*A61B 1/05* (2006.01)
*A61B 17/50* (2006.01)
*A61B 17/22* (2006.01)
*A61B 10/02* (2006.01)
*A61B 17/34* (2006.01)

(52) U.S. Cl.
CPC .............. *A61B 1/018* (2013.01); *A61B 1/05* (2013.01); *A61B 10/0233* (2013.01); *A61B 10/04* (2013.01); *A61B 17/22031* (2013.01); *A61B 17/3478* (2013.01); *A61B 17/50* (2013.01); *A61B 2010/045* (2013.01); *A61B 2017/00327* (2013.01); *A61B 2017/00349* (2013.01); *A61B 2017/00367* (2013.01); *A61B 2017/22035* (2013.01); *A61B 2217/005* (2013.01); *A61B 2217/007* (2013.01)

(58) Field of Classification Search
USPC ................................ 600/104, 106, 562, 564
See application file for complete search history.

(56) References Cited

U.S. PATENT DOCUMENTS

| | | | |
|---|---|---|---|
| 5,938,603 A * | 8/1999 | Ponzi | A61M 25/0147 600/424 |
| 5,984,932 A | 11/1999 | Yoon | |
| 6,296,608 B1 | 10/2001 | Daniels | |
| 6,419,626 B1 | 7/2002 | Yoon | |
| 6,620,122 B2 | 9/2003 | Richardson | |
| 6,648,910 B1 | 11/2003 | Bergeron | |
| 6,780,175 B1 | 8/2004 | Sachdeva | |
| 7,169,167 B2 | 1/2007 | Chu | |
| D556,760 S | 12/2007 | Ashida et al. | |
| 7,413,543 B2 | 8/2008 | Fantone | |
| 7,662,089 B2 | 2/2010 | Okada | |
| D628,692 S | 12/2010 | Greenhalgh | |
| 7,846,107 B2 | 12/2010 | Rowland | |
| 7,922,652 B2 | 4/2011 | Yagi | |
| 8,007,508 B2 | 8/2011 | Cox | |
| D650,480 S | 12/2011 | Scholly | |
| D674,486 S | 1/2013 | Onuma | |
| D683,022 S | 5/2013 | Moon et al. | |
| D702,358 S | 4/2014 | Shinohara et al. | |
| D719,651 S | 12/2014 | Hoffmann et al. | |
| 9,005,186 B2 | 4/2015 | Machill | |
| D733,290 S | 6/2015 | Burton et al. | |
| D738,516 S | 9/2015 | Karim | |
| D740,411 S | 10/2015 | Lee-Sepsick | |
| D757,953 S | 5/2016 | Philips | |
| D772,406 S | 11/2016 | Sanso et al. | |
| D776,810 S | 1/2017 | Tseng et al. | |
| D777,321 S | 1/2017 | Nakagami et al. | |
| 2002/0143387 A1 | 10/2002 | Friedland | |
| 2003/0139647 A1* | 7/2003 | Raz | A61B 1/0008 600/104 |
| 2004/0138525 A1* | 7/2004 | Saadat | A61B 1/0055 600/104 |
| 2005/0119668 A1 | 6/2005 | Desmond | |
| 2006/0258955 A1 | 11/2006 | Hoffman et al. | |
| 2008/0021276 A1 | 1/2008 | Wax | |
| 2008/0027464 A1 | 1/2008 | Barbagli | |
| 2008/0071144 A1 | 3/2008 | Fein | |
| 2008/0207996 A1 | 8/2008 | Tsai | |
| 2009/0023989 A1 | 1/2009 | Ichikawa | |
| 2009/0259141 A1* | 10/2009 | Ewers | A61B 1/00098 600/562 |
| 2009/0292164 A1* | 11/2009 | Yamatani | A61B 1/00087 600/106 |
| 2009/0326384 A1 | 12/2009 | Singh | |
| 2010/0217258 A1 | 8/2010 | Floume | |
| 2011/0063428 A1 | 3/2011 | Sonnenschein | |
| 2011/0065985 A1* | 3/2011 | Wehrheim | A61B 1/0008 600/106 |
| 2011/0125054 A1* | 5/2011 | Clements | A61B 10/0266 600/566 |
| 2011/0218400 A1* | 9/2011 | Ma | A61B 1/05 600/109 |
| 2011/0288372 A1* | 11/2011 | Petersen | A61B 1/0008 600/109 |
| 2013/0165909 A1 | 6/2013 | Machill | |
| 2013/0314516 A1 | 11/2013 | Uchihara | |
| 2016/0081539 A1 | 3/2016 | Pagan | |
| 2016/0242629 A1 | 8/2016 | Hijihara et al. | |

FOREIGN PATENT DOCUMENTS

| | | |
|---|---|---|
| EP | 1512366 A1 | 3/2005 |
| EP | 2123225 A1 | 11/2009 |
| EP | 2294967 A1 | 3/2011 |
| FR | 2860705 B1 | 7/2006 |
| WO | 2008015666 A2 | 2/2008 |

\* cited by examiner

OPERATING DEVICE WITH A CONTROL HANDLE AND A FLEXIBLE ELEMENT CONNECTED TO THE CONTROL HANDLE

TECHNICAL FIELD

The present invention relates to an operation device especially intended for proceeding to an operation inside the body of a living being, this device comprising a control handle and a flexible element provided with a proximal end connected to this control handle, the flexible element comprising at a distal end, a steerable area comprising a rigid head, the control handle comprising a control lever arranged for controlling said steerable area of this flexible element.

BACKGROUND ART

There are currently different devices achieved for acting in a relatively non-invasive manner inside the body of a living being. These devices comprise endoscopes and the related devices allowing a particular use, such as cystoscopes, bronchoscopes, gastroscopes, etc.

Usually, with this kind of devices, with which it is necessary to operate inside the body of a living being, especially a human, an endoscope having a flexible part provided with a steerable area equipped with a camera is used. The flexible part of the endoscope is introduced to reach the work area or the area wherein the operation has to be carried out, a tool is then introduced in a channel of the flexible part of the endoscope, this tool being used to proceed with the desired operation.

This kind of devices has a number of drawbacks. In particular, when the endoscope is reusable, it has to be sterilized in a particularly secure way in order to avoid any contamination from another patient. This sterilization is generally complex and requires much time and expensive material. Moreover, in order to have a sterilizable instrument, it is necessary to make it from materials designed for such sterilization operations. Such materials, as well as devices made in the same way, are usually relatively expensive.

Moreover, the fact of introducing a tool inside the endoscope channel involves a relatively large diameter of this channel. In practice, a channel having a minimum possible diameter is obviously being sought, so as to be the least unpleasant, painful or invasive for the patient.

There are also endoscopes, equipped at their flexible end, with tools intended to enable a determined operation. Such an endoscope is disclosed, for example in the patent application EP 2 123 225. This document refers to an endoscope comprising tools arranged at the flexible end of the endoscope. These tools are fixed. This might present different problems. In fact, the introduction of the endoscope in a patient to the work area may be made more difficult due to the presence of these tools. Moreover, the tools are partially positioned in front of the camera. Thus, they can hide some areas to the camera, which is undesirable.

This invention intends to provide an endoscope avoiding the drawbacks of the prior art devices, in particular by carrying out an endoscopy apparatus allowing an effective and simple manipulation, with a minimum diameter of the flexible part.

DISCLOSURE OF THE INVENTION

The object of the invention is achieved by an operation device as defined in the preamble and characterized in that the flexible element comprises a retractable tool at its distal end, this retractable tool being arranged to be operated by said control handle.

In the present invention, the retractable tool is an integral part of the device. As a result, it is unnecessary to join it to this device and it is also unnecessary to use a tube having a relatively large diameter in order to allow a tool to slide into the same. This embodiment allows obtaining relatively low manufacturing costs, compatible with a single-use instrument.

Additional advantages can be obtained with a retractable tool. Indeed, when the tool is retracted, the introduction of the endoscope is easier since there is no element exceeding the head and obstructing the displacement of the device.

Moreover, the field of view of the camera arranged at the end of the endoscope head is not limited by the presence of a tool. Therefore the device thus obtained is easier to be put in place thanks to a diameter smaller than the majority of the similar devices of the prior art, thanks to a head from which no element obstructing the introduction exceeds and to an optimal view by means of the camera. When the end of the device is in place, the tool can be used in a conventional way in order to carry out the desired operation.

BRIEF DESCRIPTION OF THE DRAWINGS

The present invention and its advantages will be better understood with reference to the enclosed drawings and to the detailed description of a particular embodiment, in which.

MODES FOR CARRYING OUT THE INVENTION

Figure 1:
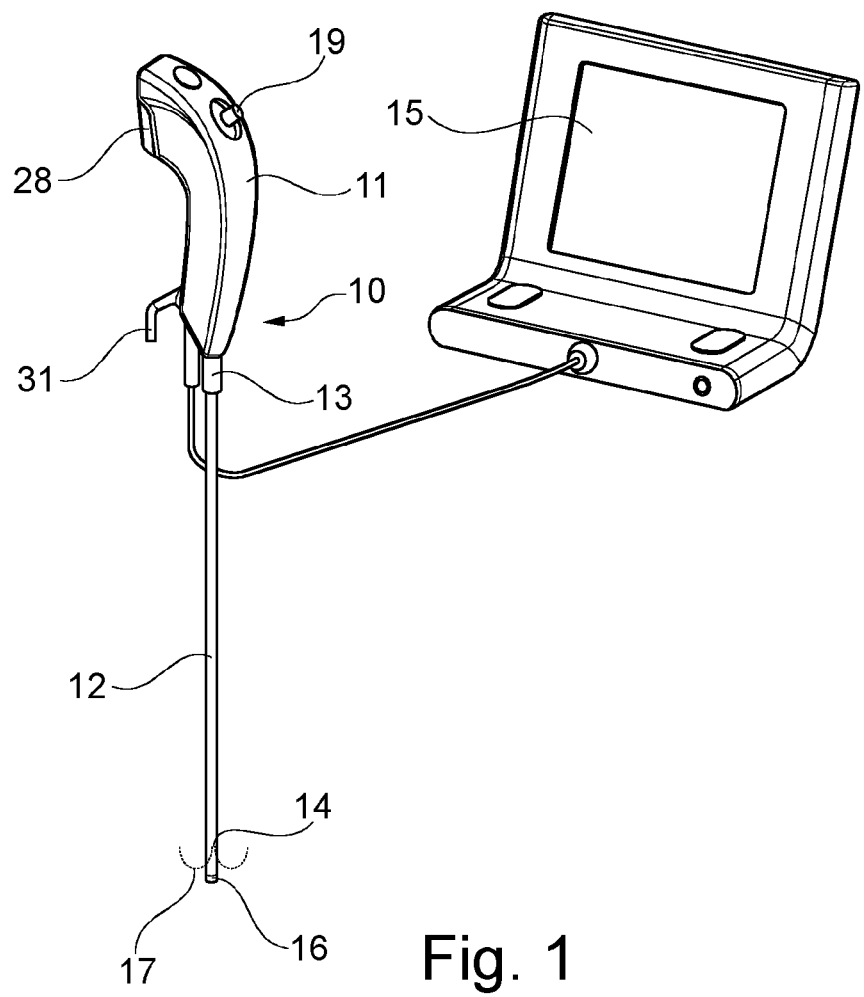
FIG. 1 is an overview of the device of the invention.
Figure 2:
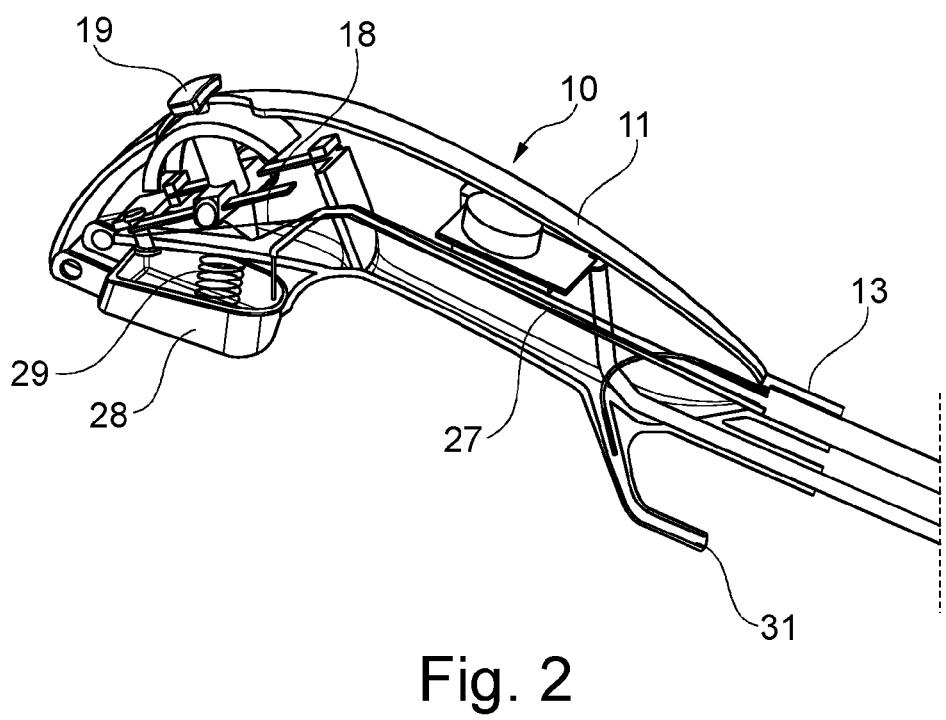
FIG. 2 is an exploded view of a part of the device of the invention.
Figure 3:
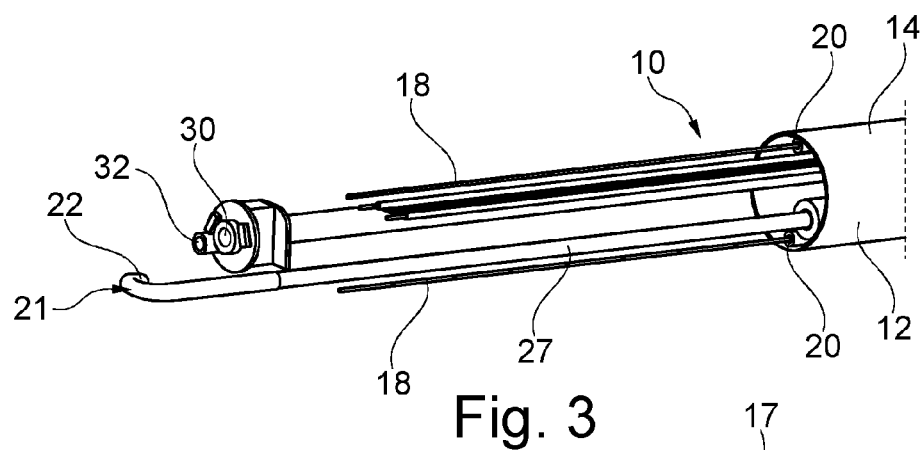
FIG. 3 is a view of a detail of the device of the invention.
Figure 4:
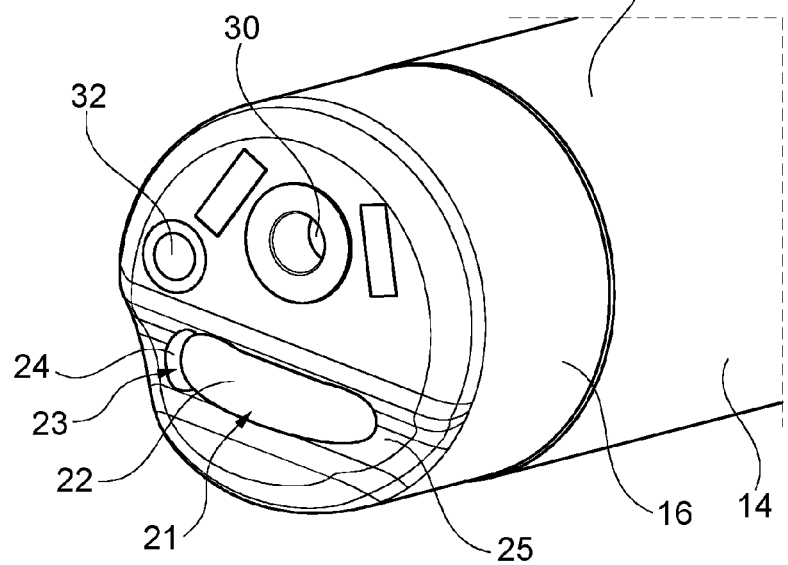
FIG. 4 is a view of a detail of an end of the device of the invention, in a first position.

With reference to the figures, and in particular to FIGS. 1 to 3, the device 10 of the invention comprises a control handle 11 and a flexible element 12. This device can be associated to a display screen 15 that can be connected through a wired or wireless connection to the control handle 11. According to a variant, a screen can also be arranged on the control handle.

The flexible element 12 comprises a proximal end 13 connected to the control handle 11 and a distal end 14, which is generally introduced inside the body of a living being in order to proceed with an operation.

This flexible element 12 is hollow and allows the passage of different elements as detailed below.

The distal end 14 of the flexible element 12 comprises a rigid head 16 placed at the end of a steerable area 17. The steerable area is connected via two cables 18 to a control lever 19 placed on the control handle. These control cables 18 are placed in tubes 20 of the flexible element and are connected in such a way that the displacement of the control lever 19 acts on the control cables, which in turn act on the steerable area 17. Thus, the steerable area can easily be remotely manipulated by activating the control lever 19 while this steerable area is moved towards the work area.

The flexible element 12 also comprises at its distal end 14, a retractable tool 21 shown in more details in FIGS. 3 to 6. In the embodiment shown in the figures, this retractable tool 21 is a hook 22. Other embodiments could also be considered, such as for instance a retractable tool made in the form of a needle or of a stylet-cannula unit used to carry out biopsies.

The hook-shaped retractable tool can have three distinctive positions. In a first position, known as retracted position, shown in FIG. 4, the tool is placed in the rigid head 16. For this purpose, this rigid head comprises a housing 23 intended to receive the retractable tool 21. This housing can for instance be formed by a blind hole 24 and a groove 25.

Figure 5:
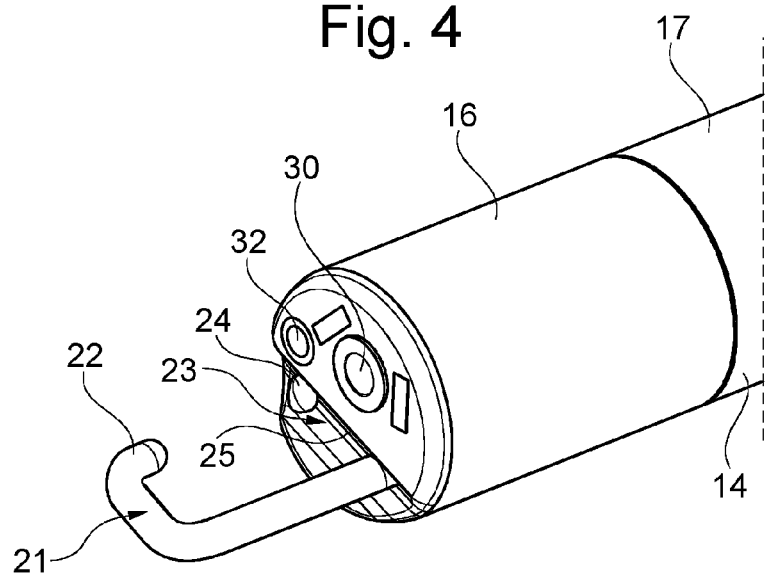
FIG. 5 is a view similar to FIG. 4, in a second position.
Figure 6:
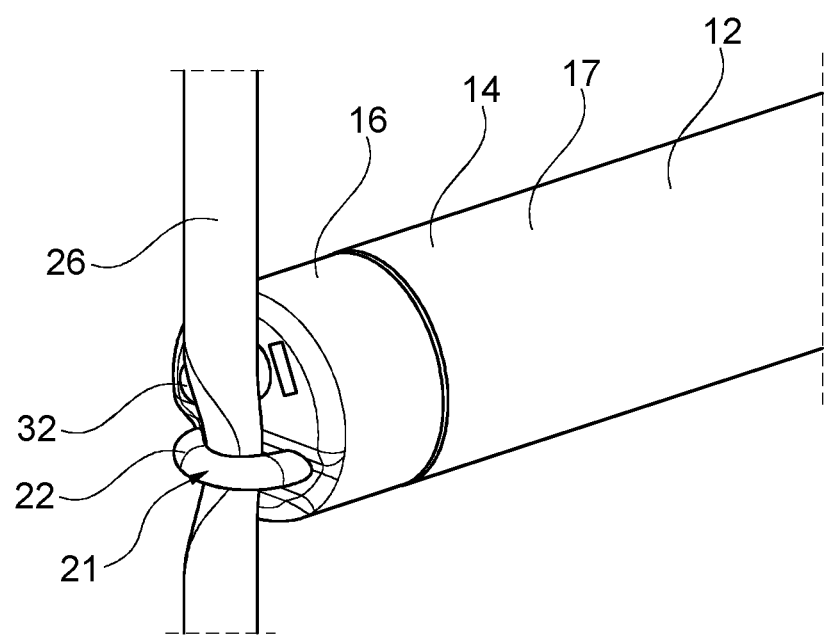
FIG. 6 is a view similar to FIGS. 4 and 5, in a third position.

In a second position, the retractable tool 21 is in an extended position, in which it is positioned outside the housing 23. In the disclosed embodiment, in extended position, a gap is created between the rigid head 16 and the hook 22, in order to place an object between the retractable tool and the head. This position is shown in FIG. 5.

In a third position, a so-called gripping position, the retractable tool 21 is pressed toward the rigid head 16 and applies a certain force directed to this head. This position allows an object 26 to be maintained between the hook 22 and the head 16 in order to be able to move this object by pulling on the device.

The retractable tool 21 is connected to the control handle 11 by a rod 27 or a cable shown on FIGS. 2 and 3. More specifically, this tool is connected to a trigger 28 arranged on the control handle 11. The trigger 28 can be positioned in a rest position and in a work position. When the trigger is positioned in the work position, the retractable tool 21 is in extended position. The work position of the trigger is obtained when a user applies a force on this trigger. When the trigger is released, i.e. when the user is no longer applying a force on said trigger, a return spring 29 tends to bring the trigger back to the rest position. The retractable tool 21 thus returns to the control handle 11, either in gripping position if an object 26 is positioned between the tool and the head, or in rest position, in the absence of object.

According to an advantageous embodiment, the rigid head 16 of the device 10 comprises a camera 30 connected to the control handle 11 via an electric connection located in the flexible element 12. This control handle may comprise display means such as a screen. The control handle may also comprise a wired or wireless connection allowing data recorded by the camera to be transmitted to an external display screen 15.

Thanks to the camera 30 and to the steerable area 17, it is possible to move the flexible element 12 and the retractable tool 21 into the area in which the operation has to be carried out. Since the retractable tool is in retracted position inside the head, this displacement becomes easier.

According to one particular embodiment, the control handle 11 comprises an injection entrance 31 that can be connected to a fluid container (not represented). This injection entrance 31 is connected to the interior of the flexible element 12 and allows to inject, in particular a liquid, into the flexible element and to convey the liquid to the distal end 14 of this flexible element. For this purpose, the head comprises at least one opening 32. This liquid injection facilitates the introduction and the displacement of the flexible element to the area in which the operation has to be carried out.

The injection entrance 31 can be connected to a container, a syringe or any other source of fluid to be injected. The fluid can be a liquid or possibly a gas. According to a particular embodiment, it is also possible to use this injection entrance for delivering a solid product, for instance in a powder form mixed with a liquid, of colloid or paste, in the area of the operation.

According to a particular embodiment of the invention, the retractable tool is a needle. In this embodiment, the rest position of the tool corresponds to a position in which the needle is fully retracted into the head. Thus, the flexible element can be set up without risk of injury in an area different from the operation area. In the extended position, the needle exceeds the head. In this embodiment, the needle is advantageously hollow and connected to a fluid entrance that may be, either the same as the injection entrance 31 or a different one. Thus, a first fluid can be used for instance in order to facilitate the displacement of the flexible element until the operation area and another fluid can be used for being injected in a living being's organ.

When the flexible element is removed, the needle is ideally put back to its rest position in order to avoid causing injury to an organ during this removal.

According to another embodiment (not represented), the retractable tool is a biopsy needle. This tool comprises a stylet, provided with at least a notch and a cannula placed around this stylet and intended to take a tissue sample and to maintain this sample trapped in said notch.

In this embodiment, the rest position corresponds to a position in which the cannula and the stylet are retracted into the head. The extended position corresponds to a position in which the sleeve is moved and exceeds the head. In this position, the cannula is located to the rear of the head so that the notch is uncovered.

The gripping position corresponds to a position in which the cannula covers the notch of the stylet, both elements can be repositioned inside the head or possibly slightly exceed the latter.

The displacement of both the needle and the sleeve can be carried out independently from each other by means of two levers placed on the control handle. However, according to one advantageous embodiment, such displacements are coordinated and carried out by means of a single lever that generates different displacements in the required order.

Obviously, other retractable tools could also be used according to the principle of the invention.

The device 10 of the invention equipped with a retractable tool 21 shaped like a hook 22 is used in particular for extracting a "stent" after a urological operation. In this case, the flexible element 12 is moved to the operation area by guiding the steerable area 17 with the control lever 19 and thanks to the images sent by the camera 30. When the retractable tool 21 is located near the stent, the trigger 28 is operated in order to move this retractable tool from the rest position into the extended position. The flexible element 12 is moved and/or pivoted by moving and/or pivoting the control handle 11 until a part of the stent is positioned between the hook 22 and the gripping area of the rigid head 16. The trigger 28 is then released. Under the effect of the return spring 29, it tends to return to its rest position. Due to the fact that a cable or a stem 27 to the retractable tool connects the latter, this tends to retract and reaches the gripping position in which the stent is jammed between the rigid head 16 and the hook 22. Removing the flexible element 12 thus allows removing the stent.

Due to the relatively simple achievement of the components of the invention device, it is possible to manufacture the same at low cost, which further allows the production of a single-use device. This implies in turn that the used materials do not have to be provided for enduring sterilization phases.

According to a variant, the retractable tool 21 could be removable in such a way that, depending on the application, it is not necessary to develop a complete device for each application, but only an adapted tool. This can be achieved provided that some mechanisms, such as for instance the activation of the trigger 28, are identical for different retractable tools. According to an advantageous embodiment, the retractable tool could have a standard fixing at the rear of the rigid head 16. In this case, it would be sufficient to change the tool in this head while keeping the rest of the device.

The invention claimed is:

1. An operating device comprising:
   a control handle comprising a displaceable control lever and a trigger;
   a flexible element having a proximal end connected to the control handle and a distal end comprising a steerable area including a rigid head and a retractable tool;
   two control cables connected between the control lever and the steerable area; and
   an actuator connected between the trigger and the retractable tool;
   wherein displacement of the control lever acts on both the cables to control movement of the steerable area of the flexible element and displacement of the trigger controls movement of the retractable tool, and
   wherein the retractable tool is a hook having an end and configured to be received in a housing of the rigid head, the housing being formed by a blind hole in an endmost surface of the rigid head and a groove in the endmost surface of the rigid head, such that, in a retracted position the hook extends from a tool hole in the housing and locates in the groove and the end of the hook locates in the blind hole, and in an extended position, the hook locates outside of and distal to the housing to create a gap between the endmost surface of the rigid head and the hook in which gap an object can be retained.

2. The operating device of claim 1, wherein the hook is removable.

3. The operating device of claim 1, wherein the trigger is movable between a rest position and a work position.

4. The operating device of claim 1, wherein the trigger is connected to a return spring arranged in order to place the trigger in a rest position and to bias the retractable tool to the retracted position when the trigger is in the rest position.

5. The operating device of claim 1, wherein the actuator connecting the hook and the trigger is a rod.

6. The operating device of claim 1, wherein the actuator connecting the hook and the trigger is a cable.

7. The operating device of claim 1, wherein, in a gripping position, the hook and the rigid head configure to maintain a urological stent between the hook and the endmost surface of the rigid head.

8. The operating device of claim 1, wherein the rigid head comprises a camera connected to the control handle via an electric connection located in the flexible element.

9. The operating device of claim 1, wherein the control handle comprises a wired connection to an external display screen.

10. The operating device of claim 1, wherein the control handle comprises a wireless connection to an external display screen.

11. The operating device of claim 1, wherein the control handle comprises an injection entrance in fluid communication with an opening of the rigid head through the flexible element.

12. The operating device of claim 1, wherein the groove is formed as a recess in the endmost surface of the rigid head, the recess configured to be open-ended at a perimeter of the endmost surface.

13. The operating device of claim 1, wherein the groove is formed as a recess in the endmost surface of the rigid head and is located perpendicular to a longitudinal direction of the operating device.

14. The operating device of claim 1, wherein the blind hole is located within the groove of the rigid head.

* * * * *